US012086403B2

(12) United States Patent
Herrmann et al.

(10) Patent No.: US 12,086,403 B2
(45) Date of Patent: Sep. 10, 2024

(54) SCROLLING PROTECTIVE FILM SYSTEM FOR TOUCHSCREEN

(71) Applicant: Xerox Corporation, Norwalk, CT (US)

(72) Inventors: Douglas K. Herrmann, Webster, NY (US); Seemit Praharaj, Webster, NY (US); Jason M. LeFevre, Penfield, NY (US); Paul J. McConville, Webster, NY (US); Chu-Heng Liu, Penfield, NY (US); Linn C. Hoover, Webster, NY (US); David A. VanKouwenberg, Avon, NY (US)

(73) Assignee: Xerox Corporation, Norwalk, CT (US)

( * ) Notice: Subject to any disclaimer, the term of this patent is extended or adjusted under 35 U.S.C. 154(b) by 523 days.

(21) Appl. No.: 17/190,501

(22) Filed: Mar. 3, 2021

(65) Prior Publication Data

US 2022/0283683 A1 Sep. 8, 2022

(51) Int. Cl.
*G06F 3/0488* (2022.01)
*B08B 1/10* (2024.01)
*G06K 15/02* (2006.01)

(52) U.S. Cl.
CPC ........... *G06F 3/0488* (2013.01); *B08B 1/10* (2024.01); *B08B 2240/00* (2013.01); *G06K 15/1809* (2013.01)

(58) Field of Classification Search
None
See application file for complete search history.

(56) References Cited

U.S. PATENT DOCUMENTS

| 8,498,103 | B2 | 7/2013 | Graneto, III |
| 8,905,107 | B2 | 12/2014 | Patel et al. |
| 9,072,351 | B2 | 7/2015 | Schroeder |
| 9,120,954 | B2 | 9/2015 | Feller |
| 10,675,817 | B2 | 6/2020 | MacDonald et al. |
| 2007/0279853 | A1 | 12/2007 | Hung et al. |
| 2008/0067418 | A1* | 3/2008 | Ross ................ A61L 2/24 250/455.11 |

(Continued)

FOREIGN PATENT DOCUMENTS

| CA | 3027467 | * | 3/2018 | ............ B41J 13/12 |
| CN | 112007188 A | * | 12/2020 | ......... A61L 2202/14 |
| JP | H1031431 | * | 2/1998 | ............. G09F 9/00 |

(Continued)

OTHER PUBLICATIONS

TWM605789U English translation, accessed on Jun. 2023. (Year: 2020).*

(Continued)

*Primary Examiner* — Eric W Golightly
*Assistant Examiner* — Arlyn I Rivera-Cordero
(74) *Attorney, Agent, or Firm* — Gibb IP Law Firm, LLC

(57) ABSTRACT

Devices include first and second frame elements having mounting points connectable to opposite ends (e.g., first end, second end) of the touchscreen. First and second rollers are connected, respectively, to the first and second frame elements. A web of transparent material is supported by and between the first and second rollers. Further, an ultraviolet light device is connected to the second frame element and is positioned to expose the web of transparent material to ultraviolet radiation to disinfect the transparent material between users.

17 Claims, 4 Drawing Sheets

(56) References Cited

U.S. PATENT DOCUMENTS

2017/0160828 A1    6/2017  Leonhard et al.
2019/0050025 A1    2/2019  Wilson et al.

FOREIGN PATENT DOCUMENTS

| TW | M605789 U | * | 12/2020 | ......... A61L 2202/14 |
| --- | --- | --- | --- | --- |
| WO | WO-2019206802 A1 | * | 10/2019 | ......... B65H 35/0066 |
| WO | WO-2021142101 A1 | * | 7/2021 | ............... A61L 2/10 |

OTHER PUBLICATIONS

CN112007188A English translation, accessed on Jun. 2023. (Year: 2020).*
JPH1031431 English translation, accessed on Jun. 2023. (Year: 1998).*
WO-2019206802-A1 English translation, accessed on Nov. 2023. (Year: 2019).*

* cited by examiner

SCROLLING PROTECTIVE FILM SYSTEM FOR TOUCHSCREEN

BACKGROUND

Systems and methods herein generally relate to touchscreen peripherals and more particularly to those that disinfect touchscreens.

Many devices have touch screens that are used by multiple users. These touch points can become areas of disease transmission between successive users. Cleaning protocols can be implemented but are dependent on individuals being responsible for cleaning the touch screens between each use.

While disinfectant wipes may be used, they need to be supplied and disposed of at the point of use. These types of solutions are not automated, create waste, and are prone to improper implementation. This issue is especially critical for the retail applications where numerous issues arise, including disposal of wipes, theft of wipes, replacement of wipes (size, cost, availability, brand, etc.), need to touch lid, wipes dry out if lid not covered, number of wipes needed per container, possible need for additional option to clean hands (i.e., hand sanitizer), touch free wipe dispense may be needed, scent issue with different brands, etc. Further, chemicals in the wipes may damage the appearance or function of the touchscreen.

SUMMARY

Embodiments herein relate to disinfection devices that protect a touchscreen. These disinfection devices are useful with, for example, printing apparatuses that have a processor, a printing engine, a user interface, etc., where the user interface has a touchscreen. The disinfection devices herein include (among other components) first and second frame elements having mounting points connectable to opposite ends (e.g., first end, second end) of the touchscreen. First and second rollers are connected, respectively, to the first and second frame elements.

A web of transparent material is supported by and between the first and second rollers. The web of transparent material has a sufficient size to cause the web of transparent material to fully cover the touchscreen when the web of transparent material is supported between the first roller and the second roller. Further, the first and second rollers are adapted to rotate through a disinfection cycle to move the web of transparent material from the first roller to the second roller (or vice versa) and move the web of transparent material across the touchscreen. More specifically, the first and second rollers are adapted to rotate and move the web of transparent material a distance that is at least equal to the width of the touchscreen (the distance between the first and second ends of the touchscreen) during each disinfection cycle.

Further, an ultraviolet light device is positioned to expose the web of transparent material to ultraviolet radiation to sanitize the web of transparent material. The ultraviolet light device is adapted to expose the web of transparent material to the ultraviolet radiation as the web of transparent material is being unwound from the first roller and/or as the web of transparent material is being wound onto the second roller.

In some examples herein, a sensor can be operatively connected (directly or indirectly connected) to the first or second frame element, for example potentially through a controller/processor. The sensor is adapted to output a signal upon detecting a change in the user of the touchscreen. This signal causes the first and second rollers to rotate through a disinfection cycle.

In one example a controller/processor can be adapted to perform a disinfection cycle and cause the first and second rollers to periodically rotate in an unwind rotational direction to periodically move only a portion of the web of transparent material from the first roller to the second roller. The controller/processor also causes the first and second rollers to rotate in a rewind rotational direction (opposite the unwind rotational direction) in response to the web of transparent material being fully unrolled from the first roller onto the second roller. The first and second rollers can, in one option, rotate in the rewind rotational direction without pausing until the web of transparent material is fully rewound on the first roller. Also, the controller/processor can limit the number of cycles the first roller and the second roller can rotate in the rewind rotational direction. After the limit for rewind cycles has been reached, the web of transparent material is replaced with new, unused transparent material.

Methods of controlling an apparatus herein support first and second rollers using, respectively, first and second frame elements that are connected to opposite ends of a touchscreen. These methods support a web of transparent material between the first and second rollers across the touchscreen.

Methods herein detect a change in the user of the touchscreen using a sensor. In response, these methods output a signal upon detecting a change of the user of the touchscreen. This signal causes the first and second rollers to rotate through a disinfection cycle in response to the signal. More specifically, this signal can cause the first and second rollers to periodically rotate in an unwind rotational direction to periodically move only a portion of the web of transparent material from the first roller to the second roller. Thus, the first and second rollers are adapted to rotate through a disinfection cycle to move the web of transparent material from the first roller to the second roller (or vice versa) and move the web of transparent material across the touchscreen. When doing so the first and second rollers are adapted to rotate and move the web of transparent material a distance that is at least equal to the width of the touchscreen (the distance between the first and second ends of the touchscreen) during each disinfection cycle.

Also, such methods expose the web of transparent material to ultraviolet radiation using an ultraviolet light device connected to the second frame element. The web of transparent material is exposed to the ultraviolet radiation as the web of transparent material is being unwound from the first roller and/or as the web of transparent material is being wound onto the second roller (or vice versa).

Further, these methods cause the first roller and the second roller to rotate in a rewind rotational direction opposite the unwind rotational direction in response to the web of transparent material being fully unrolled from the first roller onto the second roller. The first roller and the second roller can, in one option, rotate in the rewind rotational direction without pausing until the web of transparent material is fully rewound on the first roller. This processing can also limit the number of cycles the first roller and the second roller can rotate in the rewind rotational direction.

These and other features are described in, or are apparent from, the following detailed description.

BRIEF DESCRIPTION OF THE DRAWINGS

Various exemplary systems and methods are described in detail below, with reference to the attached drawing Figs., in which.

DETAILED DESCRIPTION

Figure 1:
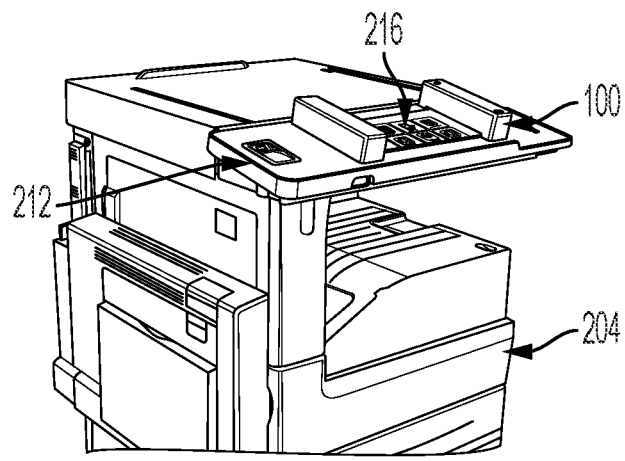
FIGS. 1 and 2 are perspective view diagrams of an apparatus having a disinfection device attached according to embodiments herein.

As mentioned above, touch points such as touchscreens can become areas of disease transmission between successive users. Cleaning protocols can be implemented but are subject to numerous disadvantages. In view of these issues, the embodiments described here provide an individualized touch screen experience so that each user has a clean disinfected surface available for the operation of the machine.

In greater detail, disinfecting apparatuses herein include two rotating cylinders located on each side of the touch screen. The rotating cylinders have wound thereon a transparent and flexible film that extends across the touch screen. When a new customer approaches the machine, the cylinders advance/index and provide a cleaned portion of the film to cover the entire touch screen. As it is wrapped up into the intake roll, the film is then treated via ultraviolet lighting to disinfect the surfaces. This process repeats each time a new customer approaches the machine and triggers the touchless sensor. A visible indicator is present on the exterior of the disinfecting apparatus to show the system is ready and disinfected. Once the transparent film has completed traversing the touch screen after many uses, the film can then be reversed to provide the treated surface film back to the other roller across the display.

This allows for the reuse of the roll for many iterations, if desired, and this makes for a green solution. The scrolls are thus reusable and not just one-time use items, which reduces waste. Further, the film can be recycled upon final use. The film can be indexed, and the number of cycles can be counted to identify when the system should have the film roll replaced. The transparent and conductive film allows the operator to contact the touch screen surface. The ultraviolet lighting can be implemented at either side (or both sides) of the roll system.

Examples of film materials used herein that are both flexible and ensure protection and accuracy on touchscreens include PET (polyethylene terephthalate), TPU (thermoplastic polyurethane), etc. These materials ensure touchscreen accuracy and are widely used for cell phone screen protection with no impact to usability. The flexible film is pressed into contact with the user interface by the user and the touch sensitivity of the screen is maintained.

This provides a solution that is completely touchless to the operator and requires no consumables other than the roll film that is replaced periodically (e.g., only after it has become worn from many reuses) which eliminates issues with manual, one time use products, such as disinfection wipes. This removes the need to dispense, store and dispose of expended wipes. The visible indicator promotes customer confidence that the surface at the touch screen has been treated prior to use, protects customer health by providing a clean interface for each use, and reduces transmission of disease in office environment and retail environments. The embodiments herein also provide competitive advantage to retail shops, introduces a green functionality by eliminating waste associated with disinfecting wipes, etc., and is a low cost technology with both rolling clear polymer lens and low-cost ultraviolet systems.

Thus, this disclosure presents an automated solution that provides continuous protection for the user of the printer touch screen. The system includes a clear film that is cycled for each new user. The clear film unrolls and scrolls from one side of the user interface to the other where it is treated by ultraviolet lights. At the point the feeding side of the scroll is depleted, the system rewinds the treated scroll back to the feed side to start again. This can either be done at one time or the process of use can be reversed so that the scroll feeds from the used, but treated, side. When the operator approaches the machine, they can trigger the cover to scroll a newly sanitized/disinfection section/portion of the transparent film over the touch screen. This can be accomplished via a touchless proximity detector, if desired. The indicator shows the operator when it is safe to use the touch screen.

FIG. 1 is a perspective view diagram of one examples of the disinfection apparatuses 100 that are herein attached to a device with a user interface 212 having a touchscreen 216, which in this example is a printing device 204, but could be any device that uses a touchscreen 216.

Figure 2:
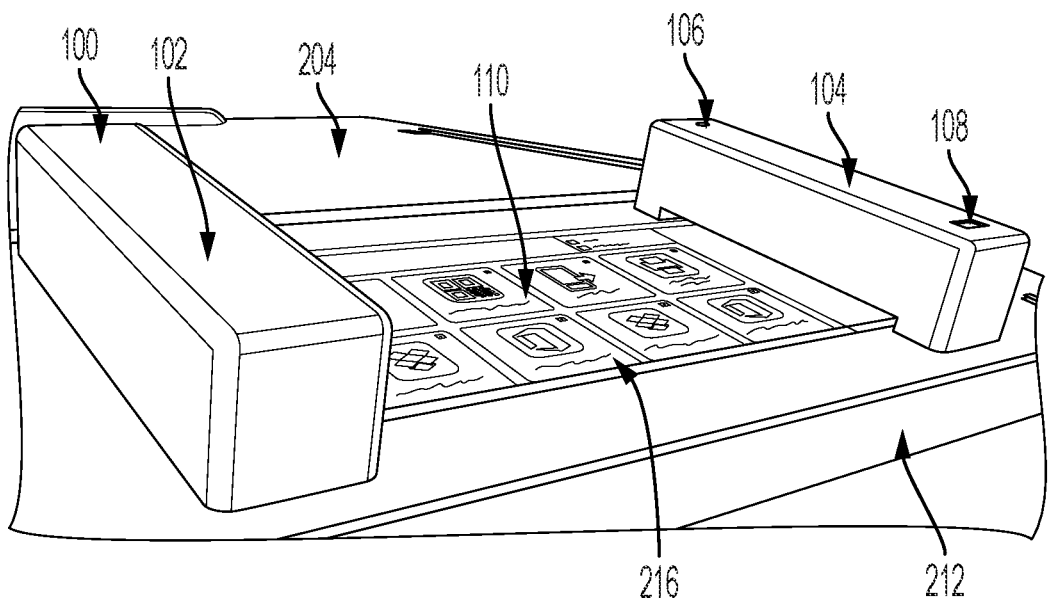

FIG. 2 is a more detailed view of the disinfection apparatus 100 attached to the touchscreen 216 shown in FIG. 1. FIG. 2 shows that the disinfection apparatus 100 herein include (among other components) first and second frame elements 102, 104 connectable to opposite ends (e.g., first end, second end) of the touchscreen 216. FIG. 2 shows a web of transparent material 110 that covers the touchscreen 216, which acts as a protective film for the touchscreen 216. Specifically, the web of transparent material 110 is disinfected and acts as a protective infection barrier between the user and the touchscreen 216 to prevent transferring viruses to and from the touchscreen 216.

FIG. 2 also shows that the disinfection apparatus 100 can include an indicator 106 (e.g., colored light, changing sign, etc.) to indicate that a disinfecting operation has been performed on the web of transparent material 110 since the previous user interacted with the touchscreen 216. In addition, FIG. 2 shows that the disinfection apparatus 100 can include a sensor 108 to detect that the user has changed or detect a user's touchless instruction for the disinfection apparatus 100 to perform a disinfecting operation on the touchscreen.

Figure 3:
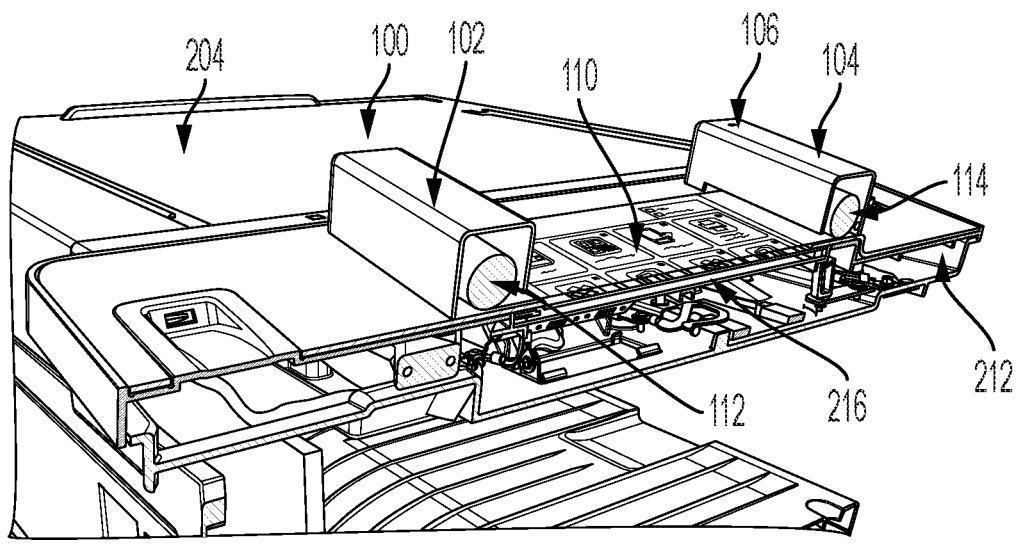
FIG. 3 is a perspective cut-away view diagram of an apparatus having a disinfection device attached according to embodiments herein.
Figure 4:
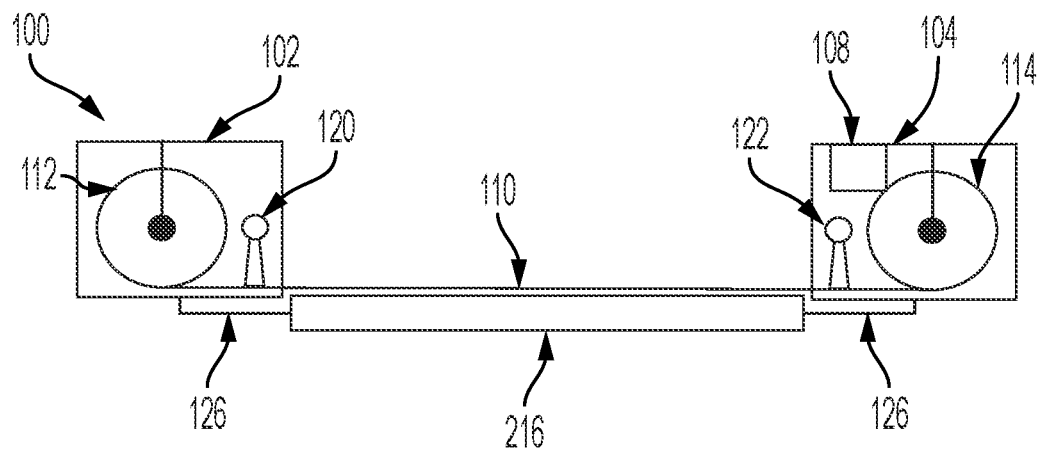
FIG. 4 is a diagram of a disinfection device connected to a touchscreen according to embodiments herein.

FIG. 3 is a cut-away view of the structure shown in FIG. 2. FIG. 3 shows first and second rollers 112, 114 that are connected, respectively, to the first and second frame elements 102, 104. FIG. 4 is a cross-sectional view which shows the touchscreen 216 and elements of the disinfection apparatus 100. FIG. 4 shows that the first and second frame elements 102, 104 have mounting points 126 connectable to opposite ends (e.g., first end, second end) of the touchscreen 216 and or other components of the user interface 212.

FIGS. 3 and 4 show that the web of transparent material 110 is supported by and between the first and second rollers 112, 114. The rollers 112, 114 include motors or other actuators that cause the rollers 112, 114 to rotate and such motors are powered by the same power source that powers the touchscreen 216 or other convenient power source. Specifically, the size (e.g., width) of the web of transparent material 110 causes the web of transparent material 110 to fully cover the height and width of the touchscreen 216 when the web of transparent material 110 is supported between the first roller 112 and the second roller 114.

Further, the first and second rollers 112, 114 are adapted to rotate through a disinfection cycle to move the web of transparent material 110 from the first roller 112 to the second roller 114 (or vice versa) and move the web of transparent material 110 across the touchscreen 216. More specifically, the first and second rollers 112, 114 are adapted to rotate and move the web of transparent material 110 a distance that is at least equal to the width of the touchscreen 216 (the distance between the first and second ends of the touchscreen 216) during each disinfection cycle.

Further, FIG. 4 shows that the disinfection apparatus 100 includes one or more ultraviolet light devices 120, 122 (e.g., incandescent or light emitting diode (LED) ultraviolet lights, etc.) that are positioned to expose the web of transparent material 110 to ultraviolet radiation to sanitize the web of transparent material 110 as the web of transparent material 110 is being wound onto or wound from the first and/or second rollers 112, 114 (and before and/or after such winding operations). The ultraviolet light device(s) 120, 122 can be attached to the first frame element 102 and/or the second frame element 104.

The ultraviolet light devices 120, 122 are adapted to expose the web of transparent material 110 to the ultraviolet radiation as the web of transparent material 110 is being unwound from the first roller 112 (ultraviolet light devices 120) and/or as the web of transparent material 110 is being wound onto the second roller 114 (ultraviolet light devices 122) and vice versa. The ultraviolet light devices 120, 122 automatically output (or are automatically controlled to output) the ultraviolet radiation at a controlled power for a controlled period of time sufficient to kill viruses and sanitize the touchscreen 216. For example, the ultraviolet radiation output by the ultraviolet light devices 120, 122 can be short-wavelength UV-C light that effectively penetrates virus cells and damages the nucleic acid, rendering the cells incapable of reproduction, or making such cells microbiologically inactive.

In some examples herein, the sensor 108 can be operatively connected (directly or indirectly connected) to the first or second frame element 102, 104, for example potentially through a controller/processor. The sensor 108 is arbitrarily shown connected to the second frame element in FIGS. 2 and 4 but could be equally connected to the first frame element 102. The sensor is adapted to output a signal upon detecting a change in the user of the touchscreen 216. This signal causes the first and second rollers 112, 114 to rotate through a disinfection cycle. In some examples, the sensor 108 can be a contact-free sensor (e.g., motion detector) that is adjusted/adapted to detect a user's wave or to detect when a previous user departs and a new user arrives, etc. Thus, in one example, the sensor 108 can be positioned to (and have a sensitivity to) detect a cycle of: a) user present; b) no user present; and c) user present, which cycle indicates a user change, which would cause the sensor to output the signal to perform a disinfection cycle.

Figure 5:
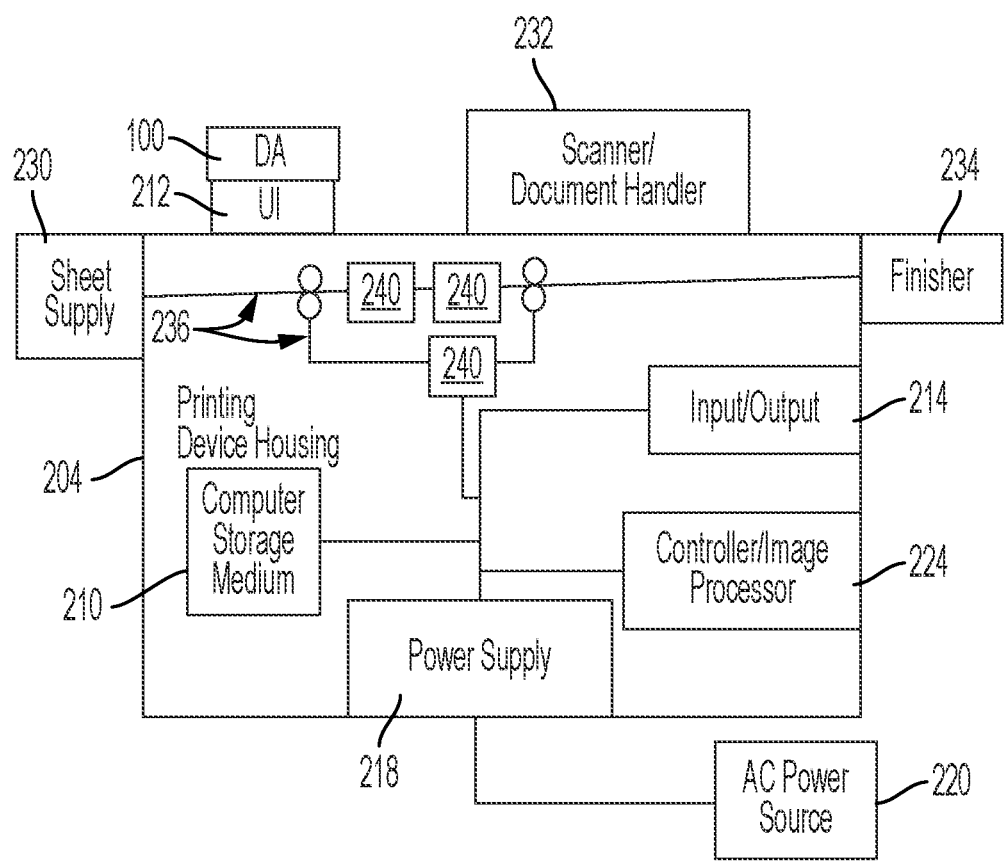
FIG. 5 is a more detailed diagram of a device having a disinfection device attached according to embodiments herein.

FIG. 5 illustrates many components of printer structures 204 herein that can comprise, for example, a printer, copier, multi-function machine, multi-function device (MFD), etc. The printing device 204 includes a controller/tangible processor 224 and a communications port (input/output) 214 operatively connected to the tangible processor 224 and to a computerized network external to the printing device 204. Also, the printing device 204 can include at least one accessory functional component, such as a user interface (UI) assembly 212. The user may receive messages, instructions, and menu options from, and enter instructions through, the user interface or control panel 212. The disinfection apparatus (DA) 100 is shown connected to the user interface 212 (e.g., specifically the touchscreen of the user interface 212) and uses the power supply of the user interface 212 or printer 204 to rotate the rollers, operate the sensor, light the indicator light, etc.

In one example, the controller/processor 224 can be adapted to perform a rotation/disinfection cycle and cause the first and second rollers 112, 114 (see FIGS. above) to periodically rotate in an unwind rotational direction to periodically move only a portion of the web of transparent material 110 from the first roller 112 to the second roller 114, using the ultraviolet light(s) 120, 122 to disinfect the web of transparent material 110 before and/or after each such periodic movement of the web of transparent material 110. The controller/processor also causes the first and second rollers 112, 114 to rotate in a rewind rotational direction (opposite the unwind rotational direction) in response to the web of transparent material 110 being fully unrolled from the first roller.

In one option, the first and second rollers 112, 114 can rotate in the rewind rotational direction without pausing until the web of transparent material 110 is fully rewound on the first roller. In other options, the first and second rollers 112, 114 can rotate in the rewind rotational direction to periodically move only a portion of the web of transparent material 110 from the second roller 114 back to the first roller 112, enabling the ultraviolet light(s) 120, 122 to disinfect the web of transparent material 110 before, during, and/or after each such periodic movement of the web of transparent material 110.

Also, the controller/processor can limit the number of cycles the first roller 112 and the second roller 114 can rotate in the rewind rotational direction. After the limit for rewinds has been reached, the tangible processor 224 outputs a message on the user interface 212 that the web of transparent material 110 needs to be replaced with new, unused transparent material 110.

The input/output device 214 is used for communications to and from the printing device 204 and comprises a wired device or wireless device (of any form, whether currently known or developed in the future). The tangible processor 224 controls the various actions of the printing device 204. A non-transitory, tangible, computer storage medium device 210 (which can be optical, magnetic, capacitor based, etc., and is different from a transitory signal) is readable by the tangible processor 224 and stores instructions that the tangible processor 224 executes to allow the computerized device to perform its various functions, such as those described herein. Thus, as shown in FIG. 5, a body housing has one or more functional components that operate on power supplied from an alternating current (AC) source 220 by the power supply 218. The power supply 218 can comprise a common power conversion unit, power storage element (e.g., a battery, etc), etc.

The printing device 204 includes at least one marking device (printing engine(s)) 240 that use marking material, and are operatively connected to a tangible processor 224 (that can be different from a general purpose computer because it can be specialized for processing image data), a media path 236 positioned to supply continuous media or sheets of media from a sheet supply 230 to the marking device(s) 240, etc. After receiving various markings from the printing engine(s) 240, the sheets of media can optionally pass to a finisher 234 which can fold, staple, sort, etc., the various printed sheets. Also, the printing device 204 can include at least one accessory functional component (such as a scanner/document handler 232 (automatic document feeder (ADF)), etc.) that also operate on the power supplied from the external power source 220 (through the power supply 218).

The one or more printing engines 240 are intended to illustrate any marking device that applies marking material (toner, inks, plastics, organic material, etc.) to continuous media, sheets of media, fixed platforms, etc., in two- or three-dimensional printing processes, whether currently known or developed in the future. The printing engines 240 can include, for example, devices that use electrostatic toner printers, inkjet printheads, contact printheads, three-dimensional printers, etc. The one or more printing engines 240 can include, for example, devices that use a photoreceptor belt or an intermediate transfer belt or devices that print directly to print media (e.g., inkjet printers, ribbon-based contact printers, etc.).

Figure 6:
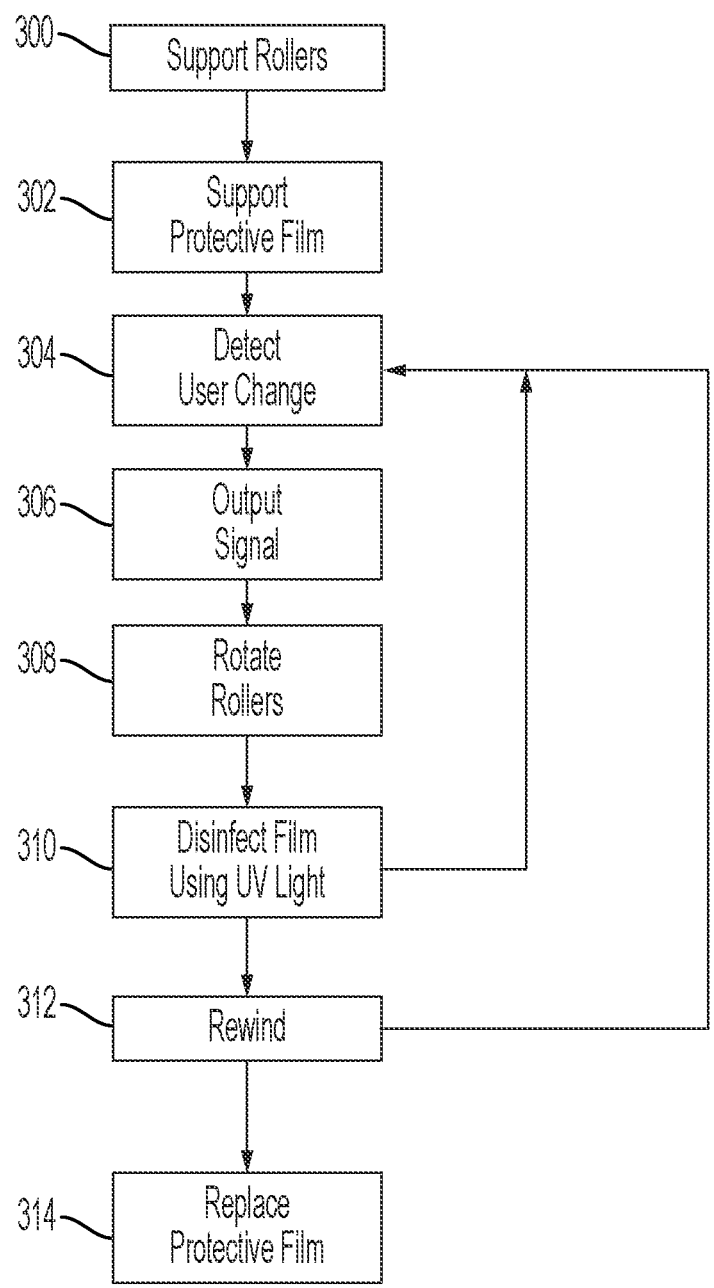
FIG. 6 is a flow diagram of various methods herein.

FIG. 6 is flowchart illustrating exemplary methods of controlling a disinfection apparatus herein, which begins by supporting first and second rollers using, respectively, first and second frame elements that are connected to opposite ends of a touchscreen in item 300. These methods support a web of transparent material (protective film) between the first and second rollers across the touchscreen in item 302. In item 304, methods herein detect a change in the user of the touchscreen using a sensor. In response, in item 306 these methods output a signal upon detecting the change of the user of the touchscreen.

This signal causes the first and second rollers to rotate through a disinfection cycle while the ultraviolet light is activated in response to the signal, in item 308. More specifically, in item 308 this signal causes the first and second rollers to periodically rotate in an unwind rotational direction to periodically move only a portion of the web of transparent material from the first roller to the second roller. Thus, in item 308, the first and second rollers are adapted to rotate through a disinfection cycle to move the web of transparent material from the first roller to the second roller (or vice versa) and move the web of transparent material across the touchscreen. More specifically, the first and second rollers are adapted to rotate and move the web of transparent material a distance that is at least equal to the width of the touchscreen (the distance between the first and second ends of the touchscreen) during each disinfection cycle.

Also, in item 310 such methods disinfect the protective film using ultraviolet (UV) light by exposing the web of transparent material to ultraviolet radiation using the ultraviolet light device(s) connected to the second frame element before, during, and/or after the web of transparent material is moved (e.g., wound/unwound). The web of transparent material is exposed to the ultraviolet radiation each time the web of transparent material is unwound from the first roller and/or each time the web of transparent material is being wound onto the second roller and vice versa. These processes are repeated between each user to ensure that each user is presented with a disinfected portion of the web of transparent material. More specifically, processing returns from item 310 to item 304 as shown by the return arrow in FIG. 6 so that the processing in items 304 through 310 is repeated for each new user to provide each new user with a disinfected portion of the web of transparent material.

Further, these methods cause the first roller and the second roller to rotate in a rewind rotational direction opposite the unwind rotational direction in response to the web of transparent material being fully unrolled from the first roller onto the second roller, as shown in item 312. In one option, the first roller and the second roller rotate in the rewind rotational direction without pausing until the web of transparent material is fully rewound on the first roller. In other options in item 312, the first and second rollers can rotate in the rewind rotational direction to periodically move only a portion of the web of transparent material from the second roller back to the first roller, enabling the ultraviolet light(s) to disinfect the web of transparent material 110 before, during, and/or after each such periodic movement of the web of transparent material 110. This processing can also limit the number of cycles the first roller and the second roller can rotate in the unwind and rewind rotational directions, after which the web of transparent material is replaced, as shown in item 314.

After the rewinding of the web of transparent material 312 (or during the rewinding 312 if the rewinding is merely a reversal of the processing direction of the web of transparent material) processing returns from item 312 to item 304 as shown by the return arrow in FIG. 6 so that the processing in items 304 potentially through 312 is repeated for each new user to provide each new user with a disinfected portion of the web of transparent material.

While some exemplary structures are illustrated in the attached drawings, those ordinarily skilled in the art would understand that the drawings are simplified schematic illustrations and that the claims presented below encompass many more features that are not illustrated (or potentially many less) but that are commonly utilized with such devices and systems. Therefore, Applicants do not intend for the claims presented below to be limited by the attached drawings, but instead the attached drawings are merely provided to illustrate a few ways in which the claimed features can be implemented.

Many computerized devices are discussed above. Computerized devices that include chip-based central processing units (CPU's), input/output devices (including graphic user interfaces (GUI), memories, comparators, tangible processors, etc.) are well-known and readily available devices produced by manufacturers such as Dell Computers, Round Rock TX, USA and Apple Computer Co., Cupertino CA, USA. Such computerized devices commonly include input/output devices, power supplies, tangible processors, electronic storage memories, wiring, etc., the details of which are omitted herefrom to allow the reader to focus on the salient aspects of the systems and methods described herein. Similarly, printers, copiers, scanners and other similar peripheral equipment are available from Xerox Corporation, Norwalk, CT, USA and the details of such devices are not discussed herein for purposes of brevity and reader focus.

The terms printer or printing device as used herein encompasses any apparatus, such as a digital copier, bookmaking machine, facsimile machine, multi-function machine, etc., which performs a print outputting function for any purpose. The details of printers, printing engines, etc., are well-known and are not described in detail herein to keep this disclosure focused on the salient features presented. The systems and methods herein can encompass systems and methods that print in color, monochrome, or handle color or monochrome image data. All foregoing systems and methods are specifically applicable to electrostatographic and/or xerographic machines and/or processes.

In addition, terms such as "right", "left", "vertical", "horizontal", "top", "bottom", "upper", "lower", "under", "below", "underlying", "over", "overlying", "parallel", "perpendicular", etc., used herein are understood to be relative locations as they are oriented and illustrated in the drawings (unless otherwise indicated). Terms such as "touching", "on", "in direct contact", "abutting", "directly adjacent to", etc., mean that at least one element physically contacts another element (without other elements separating the described elements). Further, the terms automated or automatically mean that once a process is started (by a machine or a user), one or more machines perform the process without further input from any user. Additionally, terms such as "adapted to" mean that a device is specifically designed to have specialized internal or external components that automatically perform a specific operation or function at a specific point in the processing described herein, where such specialized components are physically shaped and positioned to perform the specified operation/function at the processing point indicated herein (potentially without any operator input or action). In the drawings herein, the same identification numeral identifies the same or similar item.

It will be appreciated that the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims. Unless specifically defined in a specific claim itself, steps or components of the systems and methods herein cannot be implied or imported from any above example as limitations to any particular order, number, position, size, shape, angle, color, or material.

What is claimed is:

1. A method of controlling an apparatus comprising:
   supporting a first roller using a first frame element connected to a first end of a touchscreen;
   supporting a second roller using a second frame element connected to a second end of the touchscreen;
   supporting a web of transparent material between the first roller and the second roller across the touchscreen;
   exposing the web of transparent material to ultraviolet radiation using an ultraviolet light device connected to the second frame element;
   causing the first roller and the second roller to periodically rotate in an unwind rotational direction to periodically move only a portion of the web of transparent material from the first roller to the second roller;
   causing the first roller and the second roller to rotate in a rewind rotational direction opposite the unwind rotational direction in response to the web of transparent material being fully unrolled from the first roller, wherein the first roller and the second roller rotate in the rewind rotational direction without pausing until the web of transparent material is fully rewound on the first roller;
   limiting the number of cycles the first roller and the second roller can rotate in the rewind rotational direction; and
   after the number of cycles exceeds a limit, outputting a message on the touchscreen that the web of transparent material needs to be replaced.

2. The method according to claim 1, wherein the exposing the web of transparent material to the ultraviolet radiation is performed at least one of:
   as the web of transparent material is being unwound from the first roller; and
   as the web of transparent material is being wound onto the second roller.

3. The method according to claim 1, further comprising:
   detecting a change of user of the touchscreen using a sensor;
   outputting a signal upon detecting the change of user of the touchscreen; and
   causing the first roller and the second roller to rotate through a disinfection cycle in response to the signal.

4. The method according to claim 1, further comprising rotating the first roller and the second roller through a disinfection cycle to move the web of transparent material from the first roller to the second roller and move the web of transparent material across the touchscreen.

5. The method according to claim 4, wherein during the rotating the first roller and the second roller are adapted to rotate and move the web of transparent material a distance at least equal to a width of the touchscreen between the first end and the second end during the disinfection cycle.

6. An apparatus comprising:
   a first frame element having mounting points connectable to a first end of a touchscreen;
   a first roller connected to the first frame element;
   a second frame element having mounting points connectable to a second end of the touchscreen;
   a second roller connected to the second frame element;
   a web of transparent material supported by and between the first roller and the second roller;
   an ultraviolet light device positioned to expose the web of transparent material to ultraviolet radiation; and
   a controller operatively connected to the first roller, the second roller, and the ultraviolet light device, wherein the controller is adapted to:
   cause the first roller and the second roller to periodically rotate in an unwind rotational direction to periodically move only a portion of the web of transparent material from the first roller to the second roller;
   cause the first roller and the second roller to rotate in a rewind rotational direction opposite the unwind rotational direction in response to the web of transparent material being fully unrolled from the first roller, wherein the first roller and the second roller rotate in the rewind rotational direction without pausing until the web of transparent material is fully rewound on the first roller; and
   limit the number of cycles the first roller and the second roller can rotate in the rewind rotational direction, wherein, after the number of cycles exceeds the limit, the controller is adapted to output a message on the touchscreen that the web of transparent material needs to be replaced.

7. The apparatus according to claim 6, wherein the ultraviolet light device is adapted to expose the web of transparent material to the ultraviolet radiation at least one of:
   as the web of transparent material is being unwound from the first roller; and
   as the web of transparent material is being wound onto the second roller.

8. The apparatus according to claim 6, wherein the web of transparent material has a size to cause the web of transparent material to fully cover the touchscreen when the web of transparent material is supported between the first roller and the second roller.

9. The apparatus according to claim 1, further comprising a sensor operatively connected to the first frame element, wherein the sensor is adapted to output a signal upon detecting a change of user of the touchscreen, and wherein the signal causes the first roller and the second roller to rotate through a disinfection cycle.

10. The apparatus according to claim 6, wherein the first roller and the second roller are adapted to rotate through a disinfection cycle to move the web of transparent material from the first roller to the second roller and move the web of transparent material across the touchscreen.

11. The apparatus according to claim 10, wherein the first roller and the second roller are adapted to rotate and move the web of transparent material a distance at least equal to a width of the touchscreen between the first end and the second end during the disinfection cycle.

12. A printing apparatus comprising:
a processor;
a printing engine operatively connected to the processor;
a user interface operatively connected to the processor, wherein the user interface comprises a touchscreen;
a first frame element having mounting points connectable to a first end of the touchscreen;
a first roller connected to the first frame element;
a second frame element having mounting points connectable to a second end of the touchscreen;
a second roller connected to the second frame element;
a web of transparent material supported by and between the first roller and the second roller;
an ultraviolet light device connected to the second frame element and positioned to expose the web of transparent material to ultraviolet radiation; and
a controller operatively connected to the first roller, the second roller, and the ultraviolet light device, wherein the controller is adapted to:
cause the first roller and the second roller to periodically rotate in an unwind rotational direction to periodically move only a portion of the web of transparent material from the first roller to the second roller;
cause the first roller and the second roller to rotate in a rewind rotational direction opposite the unwind rotational direction in response to the web of transparent material being fully unrolled from the first roller, wherein the first roller and the second roller rotate in the rewind rotational direction without pausing until the web of transparent material is fully rewound on the first roller; and
limit the number of cycles the first roller and the second roller can rotate in the rewind rotational direction, wherein, after the number of cycles exceeds the limit, the controller is adapted to output a message on the touchscreen that the web of transparent material needs to be replaced.

13. The printing apparatus according to claim 12, wherein the ultraviolet light device is adapted to expose the web of transparent material to the ultraviolet radiation at least one of:
as the web of transparent material is being unwound from the first roller; and
as the web of transparent material is being wound onto the second roller.

14. The printing apparatus according to claim 12, wherein the web of transparent material has a size to cause the web of transparent material to fully cover the touchscreen when the web of transparent material is supported between the first roller and the second roller.

15. The printing apparatus according to claim 12, further comprising a sensor operatively connected to the first frame element, wherein the sensor is adapted to output a signal upon detecting a change of user of the touchscreen, and wherein the signal causes the first roller and the second roller to rotate through a disinfection cycle.

16. The printing apparatus according to claim 12, wherein the first roller and the second roller are adapted to rotate through a disinfection cycle to move the web of transparent material from the first roller to the second roller and move the web of transparent material across the touchscreen.

17. The printing apparatus according to claim 16, wherein the first roller and the second roller are adapted to rotate and move the web of transparent material a distance at least equal to a width of the touchscreen between the first end and the second end during the disinfection cycle.

\* \* \* \* \*